United States Patent
Howorth et al.

(10) Patent No.: US 8,124,022 B2
(45) Date of Patent: Feb. 28, 2012

(54) MOUNTING MATS AND POLLUTION CONTROL DEVICES USING SAME

(75) Inventors: Gary F. Howorth, Oakdale, MN (US); Javier E. Gonzalez, Oakdale, MN (US); Claus Middendorf, Neuss (DE)

(73) Assignee: 3M Innovative Properties Company, St. Paul, MN (US)

( * ) Notice: Subject to any disclaimer, the term of this patent is extended or adjusted under 35 U.S.C. 154(b) by 629 days.

(21) Appl. No.: 11/721,412

(22) PCT Filed: Nov. 30, 2005

(86) PCT No.: PCT/US2005/043265
§ 371 (c)(1),
(2), (4) Date: Apr. 9, 2009

(87) PCT Pub. No.: WO2006/065534
PCT Pub. Date: Jun. 22, 2006

(65) Prior Publication Data
US 2009/0208385 A1    Aug. 20, 2009

Related U.S. Application Data

(60) Provisional application No. 60/635,604, filed on Dec. 13, 2004, provisional application No. 60/697,821, filed on Jul. 8, 2005.

(51) Int. Cl.
*B01D 50/00* (2006.01)
(52) U.S. Cl. ..................................... 422/179
(58) Field of Classification Search ............... 428/920
See application file for complete search history.

(56) References Cited

U.S. PATENT DOCUMENTS

| | | |
|---|---|---|
| 2,624,658 A | 1/1953 | Parker at al. |
| 2,718,461 A | 9/1955 | Parker et al. |
| 3,001,571 A | 9/1961 | Hatch |
| 3,458,329 A | 7/1969 | Owens et al. |
| 3,498,774 A | 3/1970 | Saffadi |
| 3,916,057 A | 10/1975 | Hatch et al. |
| 4,038,214 A | 7/1977 | Gotoh et al. |
| 4,305,992 A | 12/1981 | Langer et al. |
| 4,385,135 A | 5/1983 | Langer et al. |
| 4,521,333 A | 6/1985 | Graham et al. |
| 5,242,871 A | 9/1993 | Hashimoto et al. |
| 5,254,410 A | 10/1993 | Langer et al. |
| 5,332,699 A | 7/1994 | Olds et al. |
| 5,585,312 A | 12/1996 | TenEyck et al. |
| 5,714,421 A | 2/1998 | Olds et al. |
| 5,736,109 A | 4/1998 | Howorth et al. |

(Continued)

FOREIGN PATENT DOCUMENTS

DE    198 58 025 A1    6/2000

(Continued)

OTHER PUBLICATIONS

Howitt et al., "Cellular Ceramic Diesel Particulate Filter", SAE Technical Paper Series No. 810114, International Congree and Exposition, Cobo Hall, Detroit, MI, Feb. 23-27, 1981.

(Continued)

*Primary Examiner* — Tom Duong

(57) ABSTRACT

Mounting materials for pollution control devices comprising biosoluble fibers, heat treated silica fibers having a silica content of greater than about 67 percent by weight (pbw) based on a total weight of the fibers, and intumescent material, with an optional binder component, are disclosed. Methods for making and using the materials are also disclosed.

22 Claims, 1 Drawing Sheet

U.S. PATENT DOCUMENTS

| | | |
|---|---|---|
| 5,853,675 A | 12/1998 | Howorth |
| 5,874,375 A | 2/1999 | Zoitos et al. |
| 6,051,193 A | 4/2000 | Langer et al. |
| 6,245,301 B1 | 6/2001 | Stroom et al. |
| 6,458,418 B2 | 10/2002 | Langer et al. |
| 6,468,932 B1 | 10/2002 | Robin et al. |
| 7,033,412 B2 | 4/2006 | Kumar et al. |
| 2004/0234436 A1 | 11/2004 | Howorth |
| 2005/0232827 A1 | 10/2005 | Merry |
| 2005/0232828 A1* | 10/2005 | Merry .......................... 422/179 |

FOREIGN PATENT DOCUMENTS

| | | |
|---|---|---|
| EP | 0 579 956 A1 | 1/1994 |
| EP | 1 388 649 A1 | 2/2004 |
| WO | WO 99/46028 | 9/1999 |
| WO | WO 00/75496 A1 | 12/2000 |
| WO | WO 03/031368 A2 | 4/2003 |
| WO | WO 2004/031544 | 4/2004 |
| WO | WO 2005/106222 | 11/2005 |

OTHER PUBLICATIONS

Brunner, "Catalytic Converter Hot Vibration Test Methods at the 3M Company", SAE International 2004-01-0146, SAE World Congress, Detroit, MI, Mar. 8-11, 2004.

* cited by examiner

MOUNTING MATS AND POLLUTION CONTROL DEVICES USING SAME

CROSS REFERENCE TO RELATED APPLICATIONS

This application is a national stage filing under 35 U.S.C. 371 of PCT/US2005/043265, filed Nov. 30, 2005, which claims priority to 60/635,604, filed Dec. 13, 2004, and 60/697,821, filed Jul. 8, 2005, the disclosure of which is incorporated by reference in its/their entirety herein.

FIELD OF THE INVENTION

The present invention relates to materials suitable for use in pollution control devices, in particular, to mats for mounting a pollution control element in a pollution control device and, more particularly, pollution control devices containing such materials.

BACKGROUND OF THE INVENTION

Pollution control devices are used on motor vehicles to reduce atmospheric pollution. Such pollution control devices include one or more pollution control elements mounted within a housing. Two types of devices are currently in widespread use: catalytic converters and diesel particulate filters or traps. Catalytic converters contain one or more catalysts, which are coated onto a substrate typically in the form of a monolithic structure. The monolithic structures are typically ceramic, although metal monoliths have been used. The catalyst(s) oxidize carbon monoxide and hydrocarbons, reduce the oxides of nitrogen in exhaust gases, or a combination thereof. Diesel particulate filters or traps typically include a wall flow filter element in the form of a honeycombed monolithic structure made from porous crystalline ceramic materials. In the current state-of-the-art construction of these pollution control devices, the monolithic structure of each type is enclosed within a housing.

A typical monolithic pollution control element generally has relatively thin walls to provide a large amount of surface area. Consequently, the structure is relatively fragile and susceptible to breakage. The typical monolithic pollution control element formed from ceramic material tends to have a coefficient of thermal expansion that is an order of magnitude less than the metal (usually stainless steel) housing or can in which it is contained. Protective packing or mounting materials such as intumescent or non-intumescent mats are typically packed between the ceramic monolith and the metal housing to avoid damage to the monolith from, for example, road shock and vibration, to compensate for the thermal expansion difference, and to prevent exhaust gases from passing between the monolith and the metal housing. The process of placing or inserting the mounting material is referred to as "canning" and includes such processes as injecting a paste into a gap between the monolith and the metal housing, or wrapping a sheet material (i.e., mounting mat) around the monolith and inserting the wrapped monolith into the housing.

Compositions used to form conventional mounting materials have included refractory ceramic fibers that can provide properties such as high temperature durability, good handling, resiliency, flexibility, and strength. Intumescent materials have also been used that volumetrically expand at elevated temperatures. Such expansion can help to hold the monolith in place during use at high temperatures. Materials that have been used for mounting pollution control elements in the housing of a pollution control device are described in, for example, Published German Patent Application No. DE 19858025 (Asglawo); and U.S. Pat. Nos. 3,916,057 (Hatch et al.); 4,305,992 (Langer et al.); 4,385,135 (Langer et al.); 5,254,410 (Langer et al.); and 5,242,871 (Hashimoto et al.).

Relatively small refractory ceramic fibers, i.e., those having a diameter of less than about 5 to 6 micrometers, have been an important component of mat compositions. However, small fibers may be troublesome in some instances. Small fibers are deemed to be respirable and are usually durable in physiological fluids, in particular, lung fluids. Thus, there is a desire for mounting mat compositions in which the use of durable, respirable refractory fibers could be avoided. It has been a significant engineering challenge, however, to make an acceptable mounting mat without this component.

Fibers that are non-durable in physiological fluids have been described in various references including U.S. Pat. No. 5,874,375 and described references therein. When such a fiber is inhaled, it decomposes in body fluids. Unfortunately, soluble inorganic fibers by themselves are not a practical substitute for refractory fibers. This lack of interchangeability can be attributed to faults that burden soluble inorganic fibers. Such fibers tend to exhibit excessive shrinkage when subjected to the temperature extremes encountered in a typical catalytic converter. Mat shrinkage can allow a fragile catalytic converter element to be loosely held inside its housing resulting in potential damage to the monolith and thus the pollution control device.

There is a continuing need for improvements to such mounting mat compositions. The present invention provides such improved compositions.

SUMMARY OF THE INVENTION

It has been found that some known mounting materials only exhibit desirable mounting properties at relatively high operating temperatures (i.e., from about 700° C. to about 950° C.). These same mounting materials exhibit less than desirable mounting properties at relatively intermediate operating temperatures (i.e., from about 400° C. to about 600° C.) and/or at relatively low operating temperatures (i.e., less than about 400° C.). The present inventors have uncovered a synergistic combination of mounting materials that together can exhibit desirable mounting properties at not only such relatively high operating temperatures, but also at relatively intermediate operating temperatures, and/or relatively low operating temperatures. Thus, the present invention addresses the need for a more universal mounting material. The present invention can also address the need for such a mounting material that avoids the use of respirable, non-decomposable refractory fibers.

In one aspect of the present invention, compositions are provided that can be used, for example, as a mounting material for mounting a pollution control element in a pollution control device. In particular, these compositions include biosoluble fibers, heat treated silica fibers having a silica content of greater than about 67 percent by weight (pbw) based on a total weight of the fibers, and intumescent material. In some embodiments, the compositions may further comprise an organic binder. The compositions can be provided, for example, in the form of a sheet material or in the form of a paste or slurry. These materials may also be useful as an insulating material positioned, for example, in one or both of the end cone regions of a pollution control device.

In another aspect of the present invention, a mounting mat is provided that is made using such compositions.

In an additional aspect of the present invention, a pollution control device is provided that includes a housing, a pollution control element disposed in the housing, and such a composition. The composition can be used as a mounting material that is disposed in a gap between at least a portion of the housing and the pollution control element. The mounting material, which is typically in the form of a paste or a sheet material, includes biosoluble fibers, heat treated silica fibers having a silica content of greater than about 67 percent by weight (pbw) based on a total weight of the fibers, intumescent material, and an optional organic binder. The mounting material can protect the fragile pollution control element from damage due to, for example, road shock and vibration, can compensate for thermal expansion differences between the pollution control element and the housing, can prevent exhaust gases from by-passing the pollution control element, or a combination thereof. The composition may also be useful as an insulation material (e.g., in the end cone regions) in the pollution control device.

In a further aspect of the present invention, a method of making a pollution control device is provided that includes a pollution control element, a housing and a mounting material. The method includes preparing a mounting material that contains biosoluble fibers, heat treated silica fibers having a silica content of greater than about 67 percent by weight (pbw) based on a total weight of the fibers, intumescent material, and an optional organic binder; placing the pollution control element in the housing; and positioning the mounting material between at least a portion of the housing and the pollution control element. The mounting material can be in the form of a sheet material or a paste.

The above summary of the present invention is not intended to describe each disclosed embodiment or every implementation of the present invention. The Figures and the detailed description that follow exemplify certain embodiments of the present invention.

BRIEF DESCRIPTION OF THE DRAWINGS

The present invention may be more completely understood in consideration of the following detailed description of various embodiments of the invention in connection with the accompanying drawings, in which.

Figure 1:
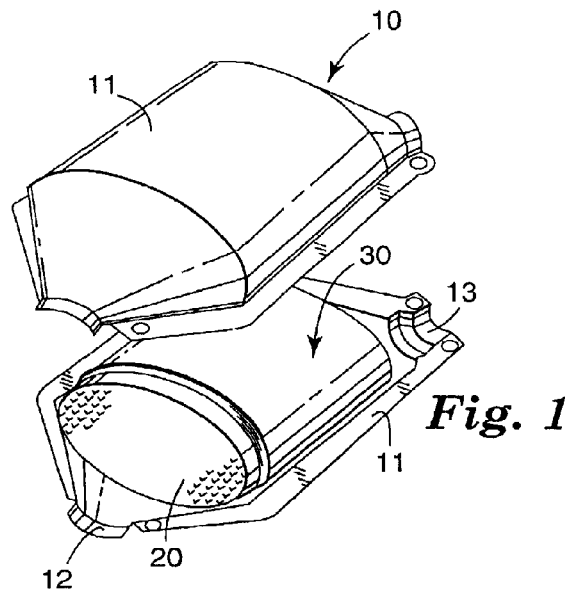
FIG. 1 is a perspective view of a catalytic converter incorporating an embodiment of the present invention and shown in disassembled relation.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

To promote an understanding of the principles of the present invention, descriptions of specific embodiments of the invention follow and specific language is used to describe the specific embodiments. It will nevertheless be understood that no limitation of the scope of the present invention is intended by the use of specific language. Alterations, further modifications, and such further applications of the principles of the present invention discussed are contemplated as would normally occur to one ordinarily skilled in the art to which the invention pertains.

The present invention is directed to compositions that may be used as mounting materials in pollution control devices. In particular, the compositions include biosoluble fibers, heat treated silica fibers having a silica content of greater than about 67 percent by weight (pbw) based on a total weight of the fibers, and intumescent material, and one or more optional binders. The compositions can be, for example, in the form of a paste but are preferably in the form of a sheet material.

The mounting material compositions can be used, for example, between the fragile monolith structure of a pollution control element and the housing of a pollution control device. That is, the compositions can be disposed in the gap between the pollution control element and the housing of a pollution control device. The compositions can be, for example, in the form of a paste or a sheet material. In one embodiment, the sheet material is in the form of a mounting mat that is wrapped around at least a portion of the pollution control element. The wrapped pollution control element is placed in the housing of the pollution control device. In another embodiment, the compositions are in the form of a paste. Such a paste may be injected or otherwise inserted into a gap in the pollution control device between at least a portion of the pollution control element and the housing. For example, the paste may be preformed (e.g., molded) into a shape desired for the gap and then inserted into the gap.

The compositions of the present invention may also be useful in pollution control devices as an insulating material. For example, the compositions may be positioned in the inlet or outlet regions (i.e., the end cone regions) of a pollution control device. For example, the inlet and/or outlet regions may each be defined by an inner end cone housing and an outer end cone housing, with the present composition disposed between the inner and outer end cone housings. The compositions may also be used to insulate the rest of the exhaust system as well as the engine from the temperatures encountered while in use. For example, one or more sections of the exhaust pipe may have a double-walled construction (i.e., an inner and outer wall), with the present composition disposed between the two walls.

When the composition is in the form of a sheet material, the sheet material can be cut or otherwise shaped to form the desired mounting mat, or insulating component (e.g., end cone), for the pollution control device. Alternatively, the composition may be molded into a desired intermediate or final shape. For example, the present composition may be molded into a flat sheet material having the desired final dimensions and then deformed into the desired final shape. For example, a molded flat mounting mat could be wrapped around the pollution control element before being installed into the pollution control device. In addition, a molded flat end cone insulation sheet could be wrapped around the inner end cone housing and then disposed within the outer end cone housing.

An illustrative example of a pollution control device in the form of catalytic converter 10 is shown in FIG. 1. The catalytic converter 10 generally includes a housing 11 surrounding a catalytic converter element 20. The housing 11 has inlet 12 and outlet 13 through which a flow of exhaust gases flows into and out of catalytic converter 10, respectively. The housing 11, which is also referred to as a can or a casing, can be made from suitable materials known in the art for such use. Typically, housing 11 includes one or more metals, metal alloys, and/or intermetallic compositions (hereinafter collectively "metals"). For example, the housing 11 can be stainless steel.

Suitable catalytic converter elements, also referred to as monoliths, are known in the art and include those made of metal, metal oxides, ceramic, or other materials. A variety of ceramic catalytic converter elements are commercially available from a variety of sources. For example, a honeycomb ceramic catalytic converter element is marketed under the trade designation "CELCOR" by Corning Inc., and another is marketed under the trade designation "HONEYCERAM" by NGK Insulated Ltd. Metal catalytic converter elements are commercially available from Emitec GmbH and Co. of Lohmar, Germany.

One or more catalyst materials can be coated onto catalytic converter element 20 in accordance with conventional practices. The catalysts used in the catalytic converter element 20 are typically one or more metals (e.g., ruthenium, osmium, rhodium, iridium, nickel, palladium, and platinum) and/or metal oxides (e.g., vanadium pentoxide and titanium dioxide). Most commonly, these catalysts function to oxidize or otherwise eliminate exhaust contaminants such as carbon monoxide and hydrocarbons. Such catalysts also can function to help reduce the amount of oxides of nitrogen in engine exhaust.

To provide a large amount of surface area, embodiments of catalytic converter element 20 generally have very thin walls. The thin walls can cause the catalytic converter element 20 to be fragile and susceptible to breakage. Additionally, in some embodiments, the catalytic converter element 20 can have a coefficient of thermal expansion about an order of magnitude less than that of housing 11. This is particularly the case when housing 11 includes a metal (usually stainless steel) and element 20 is a ceramic. The difference in thermal properties can subject catalytic converter element 20 to a risk of damage with changes in temperature. Mounting mat or sheet material 30, disposed between housing 11 and element 20, helps protect element 20 from damage due to, for example, road shock and vibration and/or the thermal expansion difference. Mounting mat or sheet material 30 also helps prevent exhaust gasses from passing between the element 20 and the metal housing 11.

Figure 2:
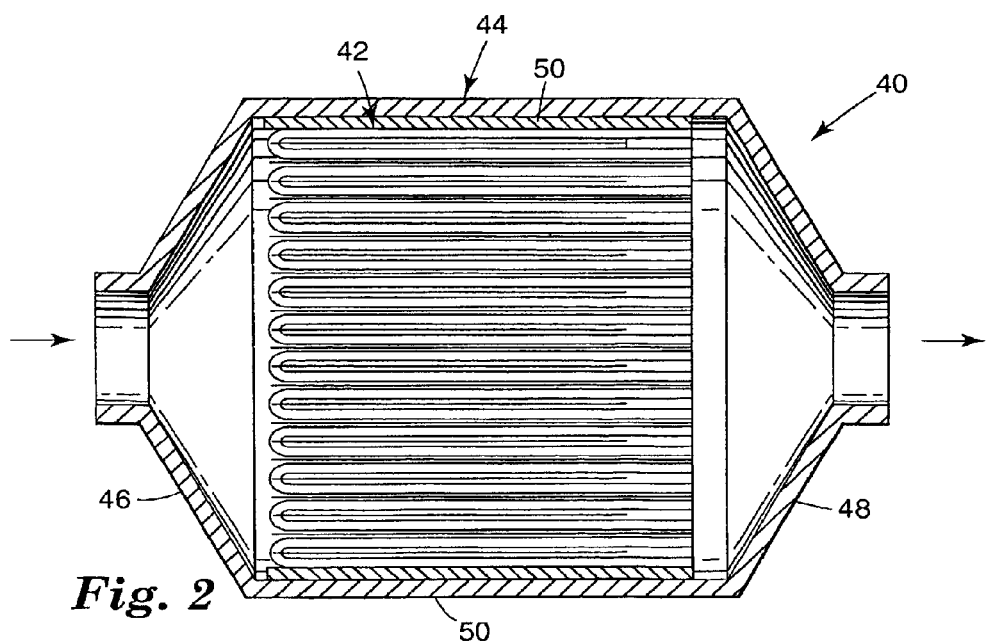
FIG. 2 is a longitudinal central section through a diesel particulate filter incorporating an embodiment of the present invention.

FIG. 2 shows a representative example of a pollution control device in the form of diesel particulate filter 40. The diesel particulate filter or trap 40 is a wall flow filter that includes a honeycombed filter element 42 having a monolithic structure with a bundle of tubes or passageways. Such diesel particulate filter elements are commercially available from a number of sources including, for example, Corning Inc. of Corning, N.Y., and NGK Insulator Ltd. of Nagoya, Japan. Useful diesel particulate filter elements are discussed in "Cellular Ceramic Diesel Particulate Filter," Howitt et al., Paper No. 810114, SAE Technical Paper Series, 1981.

A catalyst may be coated onto the filter structure 42 mounted in the diesel particulate filter 40. The diesel particulate filter 40 includes a housing 44 having inlet 46 and outlet 48. Housing 44 surrounds particulate filter element 42 (also referred to as a monolith or monolithic structure). Mounting mat or sheet material 50 is disposed between the filter element 42 and the metal housing 44 and provides the same benefits as mounting sheet 30 of FIG. 1.

Relatively small refractory ceramic fibers, i.e., those having an average diameter of less than about 5 to 6 micrometers and length greater than about 5 micrometers, have been an important component of known mounting mat compositions for pollution control devices. However, fibers in this size range can be respirable and are often durable in physiological fluids, in particular, lung fluids. Thus, mounting material compositions lacking durable, respirable, refractory ceramic fibers can be desired. It has been a significant engineering challenge, however, to make acceptable sheet materials, such as mounting mats for pollution control devices, without the durable, respirable, refractory ceramic fibers. Additionally, ceramic fiber compositions alone, while having good temperature resistance, can have unsuitable resiliency and can have difficulty in providing acceptable durability at temperatures below which a sufficient holding force is generated by an intumescent component.

As used herein, the term "fiber" refers to materials having a length that is greater than its width or diameter. In some embodiments, the length is at least 10 times, at least 100 times, or at least 1000 times the width or diameter.

As used herein, the term "respirable" refers to fibers that can be inhaled by an animal into the lungs of the animal. Typically, respirable fibers have an average diameter less than about 5 micrometers. In some embodiments, respirable fibers have an average diameter less than about 3 micrometers. Conversely, as used herein, the term "non-respirable" refers to fibers that cannot be inhaled by an animal into the lungs of the animal. Typically, non-respirable fibers have an average diameter of at least about 3 micrometers. In some embodiments, non-respirable fibers have an average diameter of at least about 5 micrometers.

I. Compositions

The compositions of the present invention comprise a number of components, which provide desired characteristics to the resulting product. Further, the compositions of the present invention have a structural configuration, which further provide desired characteristics to the resulting product. A description of composition components and structural configuration is given below.

A. Composition Components

The compositions of the present invention include an intumescent material, biosoluble fibers, heat treated silica fibers and may also include one or more optional fibers, binders and other additives. A description of each class of components is given below.

1. Intumescent Materials

The compositions of the present invention comprise one or more intumescent materials. A composition containing one or more intumescent materials can expand when heated and can typically exert sufficient pressure between a pollution control element and the housing of the pollution control device to form a supportive, protective seal when used as a mounting material. In some embodiments, such a composition can remain resiliently compressible such that the pollution control element is cushioned against physical shocks.

Examples of suitable intumescent materials can include unexpanded vermiculite, vermiculite ore, hydrobiotite, water-swellable synthetic tetrasilicic fluorine type mica described in U.S. Pat. No. 3,001,571 (Hatch), alkali metal silicate granules as described in U.S. Pat. No. 4,521,333 (Graham et al.), expandable graphite, combinations of these, and the like. Other suitable intumescent materials include, for example, granules sold by 3M (St. Paul, Minn.) under the trade designation "EXPANTROL 4BW". Some of these intumescent materials can exhibit more than 10 percent free expansion in thickness when heated to temperatures above about 200° C. or about 300° C. Additionally, some of these intumescent materials can exhibit more than about 50 percent free expansion when heated.

The intumescent materials used in the present invention desirably have an average particle size greater than about 300 micrometers (μm). In some embodiments, a portion of the intumescent material may have a particle size less than 300 μm, but greater than 150 μm (i.e., the particles do not pass through a 100 mesh screen). Typically, the intumescent materials have an average particle size ranging from greater than about 300 µm to about 2000 µm. In one desired embodiment, the intumescent materials used in the present invention have an average particle size ranging from greater than about 300 µm to about 800 m.

The amount of intumescent material included in the compositions can vary over a wide range. Typically, intumescent material is present in the composition in an amount of up to about 80 percent by weight (pbw) (or up to about 70, 60, 50, 40, 30, 20, or 10 pbw), based on a total dry weight of the composition. In one exemplary embodiment, the composition includes from greater than 0 to about 80 pbw, about 10 to about 70 pbw, about 25 to about 60 pbw, or about 35 to about 50 pbw of one or more intumescent materials based on the total dry weight of the composition.

2. Fibers

The compositions of the present invention comprise one or more types of fibers as described below.

a. Biosoluble Fibers

The compositions of the present invention comprise biosoluble fibers. As used herein, "biosoluble fibers" refers to fibers that are decomposable in a physiological medium or a simulated physiological medium. Physiological medium includes, but is not limited to, those bodily fluids typically found in the respiratory tract such as, for example, the lungs of animals or humans. As used herein, "durable" refers to fibers that are not biosoluble.

Biosolubility can be estimated by observing the effects of direct implantation of the fibers in test animals or by examination of animals or humans that have been exposed to fibers. Biosolubility can also be estimated by measuring the solubility of the fibers as a function of time in simulated physiological medium such as saline solutions, buffered saline solutions, or the like. One such method of determining solubility is described in U.S. Pat. No. 5,874,375 (Zoitas et al.).

Typically, biosoluble fibers are soluble or substantially soluble in a physiological medium within about 1 year. As used herein, the term "substantially soluble" refers to fibers that are at least about 75 weight percent dissolved. In some embodiments, at least about 50 percent of the fibers are soluble in a physiological medium within about six months. In other embodiments, at least about 50 percent of the fibers are soluble in a physiological fluid within about three months. In still other embodiments, at least about 50 percent of the biosoluble fibers are soluble in a physiological fluid within at least about days. For example, the fibers can be certified by the Fraunhofer Institut as passing the tests for the biopersistence of high temperature insulation fibers in rats after intratracheal instillation (i.e., the fibers have a halftime less than 40 days).

Yet another approach to estimating the biosolubility of fibers is based on the composition of the fibers. For example, Germany classifies respirable inorganic oxide fibers based on a carcingenicity index (KI value). The KI value is calculated by a summation of the weight percentages of alkaline and alkaline-earth oxides and subtraction of two times the weight percent of aluminum oxide in inorganic oxide fibers. Inorganic fibers that are biosoluble typically have a KI value of about 40 or greater.

In one desired embodiment of the present invention, the biosoluble fibers comprise biosoluble inorganic fibers. Biosoluble inorganic fibers suitable for use in the present invention typically include, but are not limited to, inorganic oxides such as, for example, $Na_2O$, $K_2O$, CaO, MgO, $P_2O_5$, $Li_2O$, BaO, or combinations thereof with silica. Other metal oxides or other ceramic constituents can be included in the biosoluble inorganic fibers even though these constituents, by themselves, lack the desired solubility but are present in low enough quantities such that the fibers, as a whole, are still decomposable in a physiological medium. Such metal oxides include, for example, $Al_2O_3$, $TiO_2$, $ZrO_2$, $B_2O_3$, and iron oxides. The biosoluble inorganic fibers can also include metallic components in amounts such that the fibers are decomposable in a physiological medium or simulated physiological medium.

In one embodiment, the biosoluble inorganic fibers include oxides of silica, magnesium, and calcium. These types of fibers are typically referred to as calcium magnesium silicate fibers. The calcium magnesium silicate fibers usually contain less than about 10 weight percent aluminum oxide. In some embodiments, the fibers include from about 45 to about 90 weight percent $SiO_2$, up to about 45 weight percent CaO, up to about weight percent MgO, and less than about 10 weight percent $Al_2O_3$. For example, the fibers can contain about 55 to about 75 weight percent $SiO_2$, about 25 to about 45 weight percent CaO, about 1 to about 10 weight percent MgO, and less than about 5 weight percent $Al_2O_3$.

In a further embodiment, the biosoluble inorganic fibers include oxides of silica and magnesia. These types of fibers are typically referred to as magnesium silicate fibers. The magnesium silicate fibers usually contain from about 60 to about 90 weight percent $SiO_2$, up to about 35 weight percent MgO (typically, from about 15 to about 30 weight percent MgO), and less than about 5 weight percent $Al_2O_3$. For example, the fibers can contain about 70 to about 80 weight percent $SiO_2$, about 18 to about 27 weight percent MgO, and less than about 4 weight percent of other trace elements.

Suitable biosoluble inorganic oxides fibers are described in U.S. Pat. Nos. 5,332,699 (Olds et al.); 5,585,312 (Ten Eyck et al.); 5,714,421 (Olds et al.); 5,874,375 (Zoitas et al.); and European Patent Application 02078103.5 filed on Jul. 31, 2002. Various methods can be used to form biosoluble inorganic fibers including, but not limited to, sol gel formation, crystal growing processes, and melt forming techniques such as spinning or blowing.

Biosoluble fibers are commercially available from Unifrax Corporation (Niagara Falls, N.Y.) under the trade designations "ISOFRAX" and "INSULFRAX." Other biosoluble fibers are sold by Thermal Ceramics (located in Augusta, Ga.) under the trade designation "SUPERWOOL." For example, SUPERWOOL 607 contains 60 to 70 weight percent $SiO_2$, 25 to 35 weight percent CaO, 4 to 7 weight percent MgO, and a trace amount of $Al_2O_3$. SUPERWOOL 607 MAX can be used at a slightly higher temperature and contains 60 to 70 weight percent $SiO_2$, 16 to 22 weight percent CaO, 12 to 19 weight percent MgO, and a trace amount of $Al_2O_3$.

Suitable biosoluble inorganic fibers for use in the present invention can have a wide range of average diameters and average lengths. Biosoluble inorganic fibers are commercially available that have an average fiber diameter in the range of about 0.05 micrometers to about 15 micrometers. In some embodiments, the biosoluble inorganic fibers have average fiber diameters in the range of about 0.1 micrometers to about 5 micrometers (i.e., the fibers are respirable fibers). As the average diameter of the biosoluble inorganic fibers decreases, an increased amount of the fiber can be incorporated into a given volume of the sheet material. Sheet materials prepared having a higher density of fibers tend to have better resiliency and flexibility. In other embodiments, the biosoluble inorganic fibers have average fiber diameters greater than about 3.0 micrometers, or greater than about 5 micrometers (i.e., the fibers are non-respirable fibers). In still other embodiments, the biosoluble inorganic fibers used to form a given composition comprise a mixture of non-respirable and respirable fibers.

The biosoluble inorganic fibers typically have an average fiber length in the range of about 0.1 centimeters to about 3 centimeters. Generally, the length of the biosoluble inorganic fibers is not critical as any selected fiber(s) can be broken down into smaller lengths during the manufacturing process, if desired.

The compositions of the present invention desirably comprise at least about 10 wt % and as much as 90 wt % biosoluble fibers based on a total dry weight of the composition. Typically, the compositions of the present invention comprise from about 16 to about 80 wt % (or from about 20 to about 80 wt %, from about 30 to about 60 wt %, from about 40 to about 50 wt %) of biosoluble fibers based on a total dry weight of the composition. In one desired embodiment, the compositions of the present invention comprise from about 20 to about 60 wt % of biosoluble fibers based on a total dry weight of the composition.

b. Heat Treated Silica Fibers

The compositions of the present invention also comprise heat treated silica fibers. As used herein, the term "heat treated silica fibers" refers to silica fibers (i) having a silica content of greater than about 67 percent by weight (pbw) based on a total weight of the fibers, and (ii) having been exposed to a heat treatment comprising exposing the fibers to a heat treatment temperature of at least about 400° C. for a heat treatment period of at least about 5 minutes. Heat treated silica fibers used in the present invention may comprise greater than about 67 pbw up to as much as 99.9 pbw silica based on a total weight of the fibers. Typically, the heat treated silica fibers comprise greater than about 67 pbw up to as much as 95.0 pbw silica based on a total weight of the fibers. In one desired embodiment, heat treated silica fibers of the present invention comprise from about 92.0 pbw to about 95.0 pbw silica, and from about 8.0 pbw to about 5.0 pbw alumina based on a total weight of the fibers.

Further, the heat treated silica fibers used in the present invention may be heat treated by exposing the fibers to a heat treatment temperature of at least about 400° C. or 500° C. (or 600° C., 700° C., 800° C., 900° C. or 1000° C., or even higher) for a heat treatment period of at least about 5 minutes (10 minutes, 15 minutes, 20 minutes, 25 minutes, 30 minutes, or any 5 minute increment up to about 60 minutes, or longer). In one exemplary embodiment, heat treated silica fibers used in the present invention are heat treated by (i) heating the fibers from room temperature to a maximum heat treatment temperature ranging from about 600° C. to about 1100° C., (ii) maintaining the maximum heat treatment temperature for a heat treatment period of about 5 to about 60 minutes (more typically about 60 minutes), and (iii) allowing the fibers to cool to room temperature. In one desired embodiment, heat treated silica fibers used in the present invention are heat treated by (i) heating the fibers from room temperature to a maximum heat treatment temperature of at least about 850° C. (desirably from about 850° C. to about 1050° C.), (ii) maintaining the maximum heat treatment temperature for a heat treatment period of at least about 60 minutes (typically about 60 minutes), and (iii) allowing the fibers to cool to room temperature.

It has been discovered that compositions containing an intumescent material and the above-described biosoluble fibers alone (i.e., without heat treated silica fibers), when used as mounting materials, can exhibit desirable mounting properties at high temperatures (i.e., from about 600° C. to about 950° C.); however, the compositions do not perform as well at intermediate temperatures (i.e., from about 400° C. to about 600° C.) and at low temperatures (i.e., less than about 400° C.). The addition of heat treated silica fibers has been discovered to improve the ability of the compositions to hold the pollution control element in position within the pollution control device at intermediate and low temperatures as shown in the Examples below.

Various methods can be used to form heat treated silica fibers including, but not limited to, leaching processes disclosed in U.S. Pat. No. 2,624,658, U.S. Pat. No. 2,718,461, and U.S. Pat. No. 6,468,932; and heat treating processes disclosed in U.S. Pat. No. 3,498,774, and U.S. Pat. No. 4,038,214; the subject matter of all of which is hereby incorporated by reference in its entirety.

Exemplary heat treated high silica content fibers are commercially available from Hitco Carbon Composites, Inc. (Gardena, Calif.) under the trade designation REFRASIL, and belChem Fiber Materials GmbH (Freiberg, GERMANY) under the trade designation BELCOTEX®. For example, the REFRASIL F100 fiber contains about 96 to 99 wt % $SiO_2$, while the BELCOTEX® fiber contains about 94.5 wt % $SiO_2$.

Suitable heat treated silica fibers for use in the present invention can have a wide range of average diameters and average lengths. Heat treated silica fibers are commercially available that have an average fiber diameter in the range of about 0.05 micrometers to about 15 micrometers. In some embodiments, the heat treated silica fibers have average fiber diameters in the range of about 5.0 micrometers to about 10.0 micrometers (i.e., the fibers are non-respirable fibers). However, in other embodiments, the heat treated silica fibers have average fiber diameters in the range of less than about 5.0 micrometers (i.e., the fibers are respirable fibers). As the average diameter of the heat treated silica fibers decreases, an increased amount of the fiber can be incorporated into a given volume of the sheet material. Sheet materials prepared having a higher density of fibers tend to have better resiliency and flexibility. In still other embodiments, the heat treated silica fibers used to form a given composition comprise a mixture of non-respirable and respirable fibers.

The heat treated silica fibers typically have an average fiber length in the range of about 0.1 centimeters to about 3 centimeters. Generally, the length of the heat treated silica fibers is not critical as any selected fiber(s) can be broken down into smaller lengths during the manufacturing process, if desired.

The compositions of the present invention comprise from greater than 0 wt % up to 99 wt % heat treated silica fibers based on a total dry weight of the composition. Typically, the compositions comprise at least about 4.0 wt % and as much as 90 wt % (or from about 10 to about 90 wt %, from about 20 to about 80 wt %, from about 30 to about 60 wt %, from about 40 to about 50 wt %) of heat treated silica fibers based on a total dry weight of the composition. The compositions of the present invention desirably comprise from about 5.0 to about 40 wt %, more desirably from about 8.0 to about 20 wt %, of heat treated silica fibers based on a total dry weight of the composition.

c. Optional Additional Fibers

The compositions may optionally include other inorganic fibers in addition to the above-described fibers. When present, the additional inorganic fibers are desirably non-respirable fibers although additional respirable fibers may also be used. Suitable additional fibers include, but are not limited to, fibers formed from ceramic materials such as ceramic oxides, ceramic nitrides, glass materials, or a combination thereof. The term "glass" as used herein refers to an amorphous, inorganic material such as an oxide having a diffuse x-ray diffraction pattern at least substantially without definite lines or other indicia of a crystalline phase.

The amount of additional inorganic fibers incorporated into the composition, when present, may vary over a wide range. Typically, compositions of the present invention can include up to about 15 weight percent additional inorganic fibers based on a total dry weight of the composition. In some embodiments, the compositions contain up to about weight percent, up to about 5 weight percent, or up to about 3 weight percent of additional inorganic fibers based on a total dry weight of the composition.

The additional inorganic fibers may have a fiber length similar to the above-described fiber length of the biosoluble fibers and the heat treated silica fibers. If the additional inorganic fibers are longer than desired when obtained from a desired source, the fibers can be chopped, cut, or otherwise processed to reduce the fiber length to a desired length. The additional inorganic fibers typically have an average length in the range of about 0.1 cm to about 1 cm.

3. Binders

The compositions of the present invention may comprise one or more binders. Suitable binders include organic binders and may include inorganic binders or a combination thereof.

In one exemplary embodiment of the present invention, the compositions include one or more polymeric or organic binders. Such binders can be used to provide added resiliency and flexibility during formation and during handling of the compositions. For example, when the composition is in the form of sheet material, such as a mounting mat for a pollution control device, the mounting mat can be wrapped more easily around the pollution control element. The operating temperatures encountered in such a device typically decompose, burn-off or otherwise eliminate the organic constituents. Thus, the organic constituents are typically transient rather than permanent components of the compositions.

Polymeric and other organic binders are particularly useful when a mounting mat is made using a wet-laid or modified papermaking process; however, a mat made using a dry-laid process may also benefit from the incorporation of such binders. One or more organic binders may be incorporated into the body of the mat and/or used as a coating for the mat. The mat may contain very small amounts of organic binder (below 1 wt %) or contain no organic binder.

Suitable polymeric binders can be thermoplastic or thermoset and can be provided as a solid in various forms or as a liquid comprising a 100 percent solids composition, a solution, dispersion, a latex, an emulsion, combinations of these, and the like. In some embodiments, the polymeric binder is an elastomer. Suitable polymers include, but are not limited to, natural rubber, copolymers of two or more copolymerizable species including styrene and butadiene, copolymers of two or more copolymerizable species including butadiene and acrylonitrile, (meth)acrylate polymers and copolymers, polyurethanes, silicones, polyesters, polyamides, cellulosic polymers, other elastomer polymers, or combinations of these.

The compositions can include about 0.1 to about 15 weight percent, about 0.5 to about 12 weight percent, or about 1 to about 10 weight percent of the organic binder on a dry weight basis.

In some embodiments, the polymer binders are acrylic- and/or methacrylate-containing latex compositions. Such latex compositions tend to burn cleanly without producing undesirable amounts of toxic or corrosive by-products. Examples of suitable acrylic emulsions include, but are not limited to, those commercially available under the trade designations "RHOPLEX HA-8" (a 44.5% by weight solids aqueous emulsion of acrylic copolymers) from Rohm and Haas (Philadelphia, Pa.) and under the trade designation "AIRFLEX 600BP" (a 55% solids ethylene vinyl acetate copolymer) from Air Products (Allentown, Pa.).

The amount of force necessary to move a mounted pollution control element (e.g., a monolithic catalytic element or carrier), along the longitudinal axis of the pollution control device (e.g., a catalytic converter) is directly related to the holding force exerted by the mounting mat on the pollution control element. With the present mounting mat formulation, it has been found that by using a binder (e.g., a silicone latex binder) that does not easily burn at the elevated operating temperatures of the pollution control device, instead of a binder (e.g., acrylic latex binders) that does, the holding force exerted by the mounting mat can be significantly increased. In this way, the amount of force needed to axially move the element can be significantly increased.

While not intending to necessarily be bound by any theory, it is believed that this difference in behavior is at least partially the result of there being a lower weight loss when using silicone binders, because the silicone can form solid $SiO_2$ when exposed to elevated temperatures, rather than being mostly burned off like with the latex binders. It also typically takes higher temperatures to burn the silicone binders. For example, silicone latex binders are generally stable up to about 200° C. and acrylic latex binders are generally stable up to about 150° C. With less mounting material loss, there is typically less of a drop in the pressure exerted by the mounting material, after the pollution control device has been operated.

For example, it has been found that a Dow Corning DC85 silicone binder burns out much later than an Airflex 600BP acrylic latex binder, whether exposed to elevated temperatures in an air or $N_2$ gas environment. For diesel engine applications, and some direct injection gasoline engine applications, the mounting mat binder is typically exposed to operating temperatures in the range of from about 200° C. to about 300° C. At such relatively low temperatures, the burning/degradation of the organic binder, especially silicone binders, is rather slow. It has been found that up to at least about 30% of the silicone binder remains in the mounting material (i.e., does not burn out), thus reducing the volume loss due to lost binder.

Polymeric fibers may also be used as a binder component in the compositions to improve the handling, flexibility, the resiliency, or a combination thereof. When the compositions are in the form of a sheet material, polymeric fibers tend to enhance processing and improve the wet strength of the sheet material. As with the polymeric binder, polymeric fibers tend to burn out (i.e., to decompose or be eliminated) after one or more heating cycles if the compositions are used in a pollution control device.

The polymer fibers can be formed from any of the above-mentioned polymers with respect to the polymeric binder. The compositions can include up to about 5 weight percent polymeric fibers on a dry weight basis. In some embodiments, the compositions includes up to about 2 or up to about 1 weight percent polymeric fiber. For example, the compositions can include about 0.1 to about 2 weight percent or about 0.2 to about 1.0 weight percent of polymeric fibers on a dry weight basis. The polymeric fibers may be staple fibers or fibrillated fibers. In one embodiment, the polymeric fibers are staple fibers in the range of about 0.5 to about 5 denier.

Suitable polymeric binders may be used alone or may be combined with additional components. Additional components may include, but are not limited to, monomers, plasticizers, fillers, tackifiers, surfactants or other modifiers.

Suitable inorganic binder materials may include, but are not limited to, colloidal particles; inorganic micaceous binders as disclosed in WO03/031368, assigned to 3M Innovative Properties Company (St. Paul, Minn.), the subject matter of which is hereby incorporated by reference in its entirety; and DIXIE CLAY® products commercially available from R.T. Vanderbilt Company, Inc. (Norwalk, Conn.). When present in the compositions of the present invention, the micaceous binder as described in WO03/031368 is present in an amount of less than about 5.0 wt % based on a total dry weight of the mat. Typically, the micaceous binder is present in an amount of less than about 2.0 wt % or 1.0 wt % based on a total dry weight of the mat. In most embodiments of the present invention, the composition does not contain any micaceous binder material.

4. Additives

The mats of the present invention may contain one or more additives to provide a desired characteristic to the resulting product. Suitable additives include, but are not limited to, plasticizers, wetting agents, defoaming agents, latex coagulants, clays, lightweight fillers, refractory fillers, metallic fibers, or combinations of these.

In some embodiments, the compositions are in the form of sheet materials, and the sheet materials include an edge protector to minimize erosion to the edges of the sheet material. Such erosion can be caused, for example, by the exhaust gas when the sheet material is used in a pollution control device. Suitable edge protectors can include, for example, a metal mesh placed on the edges of the sheet or a mixture of a binder and glass as disclosed in U.S. Pat. No. 6,245,301 (Stroom et al.). Other edge protectors know in the art can be used.

B. Composition Structural Configurations

The above-described composition components used in the present invention may be configured into a single sheet or may form one or more layers of a multi-layered article.

In one desired embodiment of the present invention, the composition is in the form of a single sheet material containing one or more of the above-described composition components. When present as a single sheet material, the composition typically has an average sheet thickness of up to about 10 cm (4 in), more typically, up to about 4 cm (1.57 in).

In other embodiments of the present invention, the composition can be in the form of a multilayered construction comprising two or more distinct layers. Each layer may be independently in the form of a sheet material having a similar or different sheet composition than other layers, a coating, a film, or any other layer. In one exemplary embodiment, the multi-layered article comprises a first sheet material containing one or more or all of the above-described composition components, and a second sheet material attached to the first sheet material, wherein the second sheet material comprises a nonwoven mat or layer of ceramic fibers (e.g., polycrystalline ceramic fibers, etc.) or glass fibers (e.g., S2 glass fibers, R glass fibers, E glass fibers, etc.). It can be desirable for a layer of ceramic fibers to be positioned between the pollution control element (e.g., catalytic element) and the first sheet material, especially when the first sheet material is exposed to hot temperatures (e.g., when the temperature of the gas going into the pollution control device is above about 900° C.). In this way, the layer of ceramic fibers can insulate and protect the first sheet material from exposure to detrimentally high temperatures (e.g., temperatures that destroy the ability of the intumescent material to expand repeatedly). It can also be desirable for a layer of the glass and/or ceramic fibers to be positioned between the first sheet material and the housing of the pollution control device, especially when the first sheet material is exposed to relatively cold temperatures (e.g., when the temperature of the gas going into the pollution control device is less than about 600° C.). In this way, the layer of glass and/or ceramic fibers can function to keep the temperature of the first sheet material hot enough so that the intumescent material in the first sheet material is at least partially activated (i.e., expanded). Alternatively, it may also be desirable for the first sheet material to be sandwiched between two layers of second sheet material. For example, a ceramic fiber layer can be positioned between the pollution control element (e.g., catalytic element) and the first sheet material and a layer of glass and/or ceramic fibers can be positioned between the first sheet material and the housing of the pollution control device. Such a sandwiched construction could be desirable when the first sheet material is exposed to relatively intermediate temperatures (e.g., when the temperature of the gas going into the pollution control device is in the range of from about 600° C. to about 900° C.).

In other embodiments of the present invention, the composition may be formed into objects having a three dimensional shape. Suitable objects having a three dimensional shape include, but are not limited to, extruded articles, die casted articles and molded articles.

II. Methods for Making Compositions

The present invention is also directed to methods for making the above-described compositions. The compositions can be formed using any of a variety of conventional fabrication techniques. One representative fabrication approach involves forming individual sheets of the above-described compositions. Multiple layers of sheet material may be laminated to one another if desired using an adhesive material (or the polymeric binder material when present). Multilayer sheet materials can also be formed as described in U.S. Pat. No. 5,853,675 (Howorth). Alternatively, the layers can be formed one on top of the other as described in U.S. Pat. No. 6,051,193 (Langer et al.).

The sheet materials prepared from the compositions of the present invention can be formed using any of a variety of suitable techniques such as, for example, a papermaking process. In one embodiment of a papermaking approach, an inorganic or polymeric binder is prepared by adding the binder material to water. The concentration and temperature can both vary over a wide range. In some embodiments, warm water, such as water at a temperature of about 30° C. to about 75° C., can be used to prepare the slurry. For example, water can be at a temperature of about 35° C. to about 45° C.

A dilute slurry can be prepared by adding water to the binder material. Biosoluble fibers and heat treated silica fibers can be added to the slurry. Any amount of shear that disperses the binder material and fibers can be used. In some embodiments, low to moderate shear for a relatively brief time, e.g., 1 second to 10 minutes or about 3 to 80 seconds, can be used to disperse the fibers. The slurry can be mixed at moderate speed to keep the solid ingredients suspended. Other ingredients such as a defoaming agent and polymeric binders can be added.

A suitable coagulating agent such as an acidifying agent can also be added. Other coagulating agents, such as one that can cause coagulation via basic means, can also be used in accordance with conventional practices. During coagulation, larger particles of the polymeric binder, when present, typically form. Any particulate matter present in the composition tends to bind to the binder and become trapped in the fiber matrix. That is, the particulate matter does not cause clogging of screens used for filtering. Binding the particulate matter to the fiber matrix facilities draining the water from the slurry and can decrease the processing time needed to prepare sheet material.

The intumescent material, desirably having an average particle size greater than about 300 micrometers, is typically added after coagulation. This particular order of addition can also facilitate dispersing the solids in the slurry and removing the water from the slurry. However, the order of addition is not critical and other orders of addition are acceptable.

The resultant slurry composition can be cast onto a suitable screen, drained, and pressed. Alternatively, the plies can be formed by vacuum casting the slurry onto a wire mesh or screen. The resultant pressed sheet material can be dried in any suitable manner, e.g., air dried or oven dried. For a more detailed description of the standard papermaking techniques employed, see, for example, U.S. Pat. No. 3,458,329 (Owens et al.).

The sheet material can be cut into a desired shape such as a shape suitable for use as a mounting mat or for use as a heat barrier (i.e., insulating material) in the end-cone region of a pollution control device. Cutting can be accomplished, for example, by using a die stamping process. The sheet materials prepared from the compositions of the invention can be reproducibly cut to satisfy stringent size tolerances. The sheet materials can exhibit suitable handling properties and are not so brittle as to crumble in one's hand. For example, the sheet materials can be easily and flexibly fitted around a pollution control element without breaking apart to form a resilient, protective, supportive seal in a pollution control device.

The compositions of the present invention can also be prepared in the form of a paste. To prepare a paste, the total solids are typically higher than about 30 percent. In some embodiments, the solids are about 30 to about 60 percent. The paste typically has a consistency and viscosity that can be injected, for example, into the gap between a pollution control element and the housing of a pollution control device. U.S. Pat. No. 5,736,109 (Howorth) describes a suitable process for making a paste. A paste can also be formed by initially forming a slurry and then removing some of the water to increase the percent solids. Further, the paste can be used to form a sheet material or a three-dimensional object. To form a sheet material or a three-dimensional object, the composition can be cast in a three-dimensional die, molded, or extruded through a die.

In yet a further embodiment of the present invention, the compositions are dry-laid along with the above-mentioned intumescent materials.

One or more single layers of composition in the form of a sheet material may be combined with other identical, similar or different layers to form multi-layered articles using known techniques. For example, additional layers may be coated onto an outer surface of the sheet material. Further, as described above, multiple layers of sheet material or other layers may be laminated to one another using an optional adhesive. Other mechanical methods of combining multiple layers of material to form multi-layered articles include, but are not limited to, needlepunching, stitching, etc.

The present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

The durability and performance of a mounting mat in a pollution control device such as, for example, a catalytic converter assembly, under simulated operating conditions, can be measured, for example, according to the test described in the SAE Paper 2004-01-0146 titled "Catalytic Converter Hot Vibration Test Methods at 3M Company", Nathan Brunner. The entire contents of the SAE paper are incorporated herein by reference.

In accordance with such testing, a mounting mat, according to each of Examples 1 to 3, is wrapped around a cylindrical cordierite monolith having an approximate diameter of 4.7 inches (about 119.4 mm), a length of about 3 inches (about 76.2 mm), and a weight of about 260 grams. The wrapped monolith is canned in a catalytic converter housing to the mount density specified in the examples, and is subjected to hot vibration testing with a gas inlet temperature of 500° C. The converter assembly is thermally conditioned for 5 cycles of heating for 2 hours with hot inlet gas and cooling for 1 hour. After conditioning, the test begins with a 4-hour cycle of 3 hours of heating, using hot inlet gas at a temperature of 500° C. while vibrating at 2.7 grms~12 dB (decibels). The cycle ends with cooling for 1 hour, which cools the assembly to about ambient temperature. The second 4-hour cycle starts at −9 dB, the third starts at −6 dB, etc. until 0 dB is reached. If the assembly is still intact, the test continues with 4-hour cycles at 0 dB until failure or until a designated time is reached, typically 72 hours or 96 hours.

Example 1

Chopped silica fibers (7 micron diameter, 6 mm length BELCOTEX® fiber, available from belChem fiber materials Gmbh, Freiburg, Germany) were heat treated by placing the fibers in a furnace at ambient temperature. The furnace was turned on with the controller set at 950° C. When the temperature in the furnace reached 950° C., the fibers were allowed to soak for 1 hour, and then the furnace was turned off. When the furnace cooled to ambient temperature, the fibers were removed for making into sheets.

A mat was prepared having a dry composition of 27 wt % heat treated silica fiber described above, 27 wt % biosoluble fiber (SUPERWOOL 607 available from Thermal Ceramic, Augusta, Ga.), 8 wt % vinyl acetate latex solids (AIRFLEX 600BP vinyl acetate latex having a solids of about 55% available from Air Products Polymers L.P., Allentown, Pa.) and 38 wt % unexpanded vermiculite.

A slurry was prepared by adding 3000 ml of tap water heated to 40° C. to a blender, adding the heat treated silica fibers, and mixing for 10 seconds. The biosoluble fibers were added and mixed on low speed for 5 seconds. The slurry was transferred to large mixing container; fibers from the blender were rinsed using 1000 ml of 40° C. tap water and added to the slurry in the container. The slurry was mixed with a propeller blade mixer at medium speed while adding three drops of defoamer (FOAMASTER 111 defoamer) and the vinyl acetate latex. When dispersed, 11.4 grams of a 50 wt % Alum solution (General Chemicals) was added and mixed for about 2 minutes. Then unexpanded vermiculite was added and mixed for 2 minutes. The slurry was poured rapidly into a sheet mold measuring 20.3 mm by 20.3 mm having an 80 mesh screen, and dewatered. The mold was opened and blotter paper was placed over the dewatered sheet and rolled eight times with a rolling pin. Fresh blotter paper was placed on each side of the sheet which was positioned between two course screens and pressed between about 414 kPa to 552 kPa for five minutes. The sheet was removed and placed in an oven at 110° C. and dried for about 60 minutes. The sheet was removed from the oven and conditioned at ambient temperature and humidity overnight.

The resulting mat was canned to a mount density of 0.76 g/cc and subjected to hot vibration testing as described above. The test reached the 0 dB level, and after 72 hours the test was discontinued. No failure was observed in the mat or the canned assembly.

A mat prepared in the same manner consisting of 54 wt % biosoluble fiber (SUPERWOOL 607), 8 wt % dried latex solids (AIRFLEX 600BP), and 38 wt % unexpanded vermiculite was canned to a mount density of 1.01 g/cc. The canned assembly was tested for robustness and failure was noted at the −6 dB level after 6.72 hours.

Example 2

Biosoluble fibers (ISOFRAX available from Unifrax) were pulped twice for 60 seconds in water heated to about 40° C. at about 1.05 percent solids by weight. The slurry was pumped to a holding tank and diluted to about 0.84% solids. The diluted slurry was pumped through a cyclone separator to a second holding tank to reduce the shot by about 20%. Silica fibers (BELCOTEX®), heat treated as described above, were pulped for 3 minutes at about 0.37 wt % solids and transferred to the tank with the biosoluble fibers and the slurry was further diluted to about 0.35 wt % by solids. The diluted slurry was heated to 40° C., and latex (AIRFLEX 600 BP) and sodium aluminate (1.18% of the weight of the fibers) were added while mixing to keep the slurry in suspension. After about 3 minutes, a 50 wt % alum solution in water (0.18 wt % alum based on the total slurry weight) was added to precipitate the latex and fibers. The slurry was then continuously pumped into a tank and mixed with unexpanded vermiculite that was metered into the slurry. The resulting slurry was pumped through a manifold onto a mesh belt. A vacuum was used to dewater the slurry and form a mat having about 30-40 wt % water. The mat was pressed with a roller and passed through a series of rotating steam heated cans to dry and form a mat having a dry composition of 31.1 wt % biosoluble fiber, 20.7 wt % heat treated silica fiber, 8.2 wt % latex solids, and 40 wt % unexpanded vermiculite.

The mat was canned to a mount density of about 0.70 g/cc and subjected to hot vibration testing as described above with an inlet gas temperature of 500° C. The test reached the 0 dB level, and after 96 hours (24 full cycles) the test was discontinued. No failure in the mat or the canned assembly was observed.

Example 3

A mat was prepared according to Example 2 except as noted. The biosoluble fibers (ISOFRAX) were pulped at 1.68 wt % solids. After the first dilution with water for shot removal, the slurry was about 1.05 wt % solids. The heat-treated silica fiber was pulped at 0.32 wt % solids, and the final slurry contained about 0.629 wt % solids. Sodium aluminate was added at a level of 1.15 wt % of the total dry fiber weight.

The resulting mat had a dry composition of 39.6 wt % biosoluble fibers, 9.9 wt % heat-treated silica fibers, 10.3 wt % latex solids, and 40.2 wt % unexpanded vermiculite. The mat was canned at a mount density of 0.70 g/cc and subjected to hot vibration testing using a hot gas inlet temperature of 500° C. The test reached the 0 dB level, and the test was discontinued after 96 hours. No failure was observed in the mat or canned assembly.

Example 4

A mat was prepared according to Example 3 except as noted. BELCOTEX® high silica content fibers were heat treated 900° C. The resulting mounting mat had a dry composition of about 10.2% by weight (wt.) of BELCOTEX® high silica content fibers, about 40.8% by wt. of ISOFRAX 1260 biosoluble fibers, about 40% by wt. of unexpanded vermiculite from Cometals, located at One Penn Plaza, New York, N.Y., and about 9% by wt. of AIRFLEX 600BP acrylic latex binder.

Example 5

An alternative mounting mat material can also be constructed as described in, and using the same components, in the above Example 4, with the exception that the acrylic latex binder is replaced with the same amount of DOW CORNING DC85 silicone binder.

It is believed that various modifications can be made to this exemplary mounting material. For example, in general, the organic binder used in the present inventive mounting material may comprise, consist of, or consist essentially of, for example, an acrylic latex binder, a silicone binder or a combination of both.

It is believed that the dry weight composition of the present inventive mounting material may be varied as much as the following: (a) in the range of from about 2% to about 80% by wt. of heat treated high silica content fiber, (b) at least some up to about 75% by wt. of biosoluble ceramic fiber, (c) in the range of from about 10% to about 75% by wt. of intumescent material (e.g., unexpanded vermiculite), and (d) in the range of from about 1% to about 15% by wt. of organic binder. The total fiber content (i.e., the combination of the silica and bio-soluble fiber) should be at least about 10% by wt.

It is believed that the dry weight composition of desirable mounting materials according to the present invention can vary as follows: (a) in the range of from about 5% to about 50% by wt. of heat treated high silica content fiber, (b) in the range of from about 10% to about 60% by wt. of biosoluble ceramic fiber, (c) in the range of from about 20% to about 70% by wt. of intumescent material (e.g., unexpanded vermiculite), and (d) in the range of from about 2% to about 12% by wt. of organic binder. The total fiber content (i.e., the combination of the silica and bio-soluble fiber) can be at least about 15% by wt.

The preferred dry weight composition of the present inventive mounting material can vary as follows: (a) in the range of from about 5% to about 5% by wt. of heat treated high silica content fiber, (b) in the range of from about 20% to about 50% by wt. of biosoluble ceramic fiber, (c) in the range of from about 25% to about 60% by wt. of intumescent material (e.g., unexpanded vermiculite), and (d) in the range of from about 4% to about 11% by wt. of organic binder. The total fiber content (i.e., the combination of the silica and bio-soluble fiber) can be at least about 30% by wt.

While the specification has been described in detail with respect to specific embodiments thereof, it will be appreciated that those skilled in the art, upon attaining an understanding of the foregoing, may readily conceive of alterations to, variations of, and equivalents to these embodiments. For example, the compositions of the present invention may also be useful as heat barriers (i.e., insulating materials), fire barriers or stops, or a combination thereof. For example, it may be useful to wrap or otherwise place the present compositions around pipes, heating devices, or structural elements such as building supports. The compositions of the present invention may also be useful around the monolithic structure of a fuel cell. Accordingly, the scope of the present invention should be assessed as that of the appended claims and any equivalents thereto.

What is claimed is:

1. A mounting mat comprising:
   (a) biosoluble fibers;
   (b) durable heat treated silica fibers having a silica content of greater than about 67 percent by weight (pbw) based on a total weight of the fibers and having been exposed to a heat treatment comprising exposing the fibers to a heat treatment temperature of at least about 400° C. for a heat treatment period of at least about 5 minutes; and
   (c) intumescent material.

2. The mat of claim 1, wherein the mat comprises:
   (a) from about 16 to about 80 wt % of biosoluble fibers;
   (b) from about 4 to about 80 wt % % of heat treated silica fibers; and
   (c) from about 10 to about 80 wt % of intumescent material, based on a total dry weight of the mat.

3. The mat according to claim 1, wherein the biosoluble fibers comprise $Na_2O$, $K_2O$, CaO, MgO, $P_2O_5$, $Li_2O$, BaO, or a combination thereof.

4. The mat according claim 1, wherein the heat treated silica fibers have been exposed to a heat treatment comprising exposing the fibers to a heat treatment temperature ranging from about 600° C. to about 1100° C. for a heat treatment period of about 5 to about 60 minutes.

5. The mat according to claim 1, wherein the heat treated silica fibers have been exposed to a heat treatment comprising exposing the fibers to a heat treatment temperature of at least about 850° C. for a heat treatment period of at least about 60 minutes.

6. The mat according to claim 1, wherein the heat treated silica fibers have a silica content ranging from about 67 pbw to about 99.9 pbw based on a total weight of the fibers.

7. The mat according to claim 1, wherein the heat treated silica fibers comprise from about 92.0 pbw to about 95.0 pbw silica and from about 8.0 pbw to about 5.0 pbw alumina based on a total weight of the fibers.

8. The mat according to claim 1, wherein the heat treated silica fibers comprise from about 96 pbw to about 99 pbw silica.

9. The mat according to claim 1, wherein the intumescent material comprises unexpanded vermiculite, expandable graphite, or a combination thereof.

10. The mat according to claim 1, wherein the intumescent material comprises unexpanded vermiculite.

11. The mat according to claim 1, wherein the mat contains less than about 5 wt % of micaceous binder material, based on a total dry weight of the mat.

12. The mat according to claim 4, wherein the mat contains less than 1 wt % of micaceous binder material, based on a total dry weight of the mat.

13. The mat according to claim 1, wherein the mat does not contain any micaceous binder material.

14. The mat according to claim 1, further comprising an organic binder.

15. The mat according to claim 14, wherein the organic binder comprises an acrylic latex binder.

16. The mat according to claim 1, wherein the heat treated silica fibers are non-respirable fibers.

17. The mat according to claim 1 in the form of a sheet material or a paste.

18. A pollution control device comprising the mat according to claim 1.

19. The pollution control device according to claim 18, wherein the mat is positioned between a housing and a pollution control element positioned within the housing.

20. The pollution control device according to claim 18, wherein the pollution control element comprises a catalytic converter.

21. The pollution control device according to claim 18, wherein the pollution control element comprises a filter element.

22. The pollution control device according to claim 18 further comprising:
   a first layer positioned between the pollution control element and the mat, or a second layer positioned between the mat and the housing, or both,
   wherein the first layer comprises ceramic fibers and the second layer comprises ceramic fibers, glass fibers or both ceramic and glass fibers.

* * * * *

UNITED STATES PATENT AND TRADEMARK OFFICE
CERTIFICATE OF CORRECTION

PATENT NO. : 8,124,022 B2
APPLICATION NO. : 11/721412
DATED : February 28, 2012
INVENTOR(S) : Gary F Howorth It is certified that error appears in the above-identified patent and that said Letters Patent is hereby corrected as shown below:

On the Title Page
Item [56], Right Column, Line 2 under "Other Publications"
Delete "Congree" and insert -- Congress --.

In the Specifications:

Column 7
Line 5, delete "m." and insert -- µm. --.
Line 46, delete "days." and insert -- 40 days. --.
Line 47, delete "Institut" and insert -- Institute --.
Line 54, delete "carcingenicity" and insert -- carcinogenicity --.

Column 8
Line 17, delete "weight" and insert -- 35 weight --.

Column 10
Line 18, delete "REFRASIL," and insert -- REFRASIL®, --.
Line 21, delete "REFRASIL" and insert -- REFRASIL® --.

Column 11
Line 8, delete "weight" and insert -- 10 weight --.

Column 13
Line 31, delete "know" and insert -- known --.

Column 16
Line 19, delete "grms~12" and insert -- grms-12 --.

Signed and Sealed this
Twenty-eighth Day of May, 2013

Teresa Stanek Rea
*Acting Director of the United States Patent and Trademark Office*

CERTIFICATE OF CORRECTION (continued)
U.S. Pat. No. 8,124,022 B2

Column 18
Line 1, delete "treated" and insert -- treated @ --.
Line 45, delete "5%" and insert -- 25% --.

In the Claims:

Column 19
Line 14, in Claim 2, delete "wt % %" and insert -- wt % --.
Line 21, in Claim 4, delete "claim" and insert -- to claim --.

Column 20
Line 8, in Claim 12, delete "4," and insert -- 1, --.